United States Patent [19]

Wakihira et al.

[11] 4,255,563

[45] Mar. 10, 1981

[54] PROCESS FOR PREPARING ANTHOCYANS FROM CORRESPONDING FLAVONOID GLYCOSIDES

[75] Inventors: Kazuo Wakihira; Satoshi Kikumoto; Hiroshi Kigawa; Osamu Nozaki, all of Shiga; Michio Minami, Moriyama, all of Japan

[73] Assignee: Shiraimatsu Shinyaku Company, Ltd., Shiga, Japan

[21] Appl. No.: 9,059

[22] Filed: Feb. 2, 1979

[30] Foreign Application Priority Data

Apr. 12, 1978 [JP] Japan .................................. 53-43700

[51] Int. Cl.³ ............................................. C07H 17/04
[52] U.S. Cl. .................................... 536/8; 204/158 R
[58] Field of Search ............................................ 536/8

[56] References Cited

U.S. PATENT DOCUMENTS 2,738,346   3/1956   Wender et al. .......................... 536/8
3,808,197   4/1974   Feuer et al. ............................. 536/8

FOREIGN PATENT DOCUMENTS 1532553   6/1968   France ........................................ 536/8

OTHER PUBLICATIONS

Robinson, "Chem. Ber." vol. 85, 19434A, pp. 85-87.
Malkin et al., "Jour. Amer. Chem. Soc.," vol. 52, pp. 2864-2867.

*Primary Examiner*—Johnnie R. Brown
*Attorney, Agent, or Firm*—Wenderoth, Lind & Ponack

[57] ABSTRACT

A process for preparing anthocyans by reducing the corresponding flavonoid glycosides with a metal and acid at temperatures not higher than 30° C. under acidic conditions, precipitating the anthocyans formed from the reduction reaction as a metal salt by neutralizing the reaction solution with an alkali and isolating the free anthocyans by decomposing the metal salt with concentrated hydrochloric acid.

3 Claims, No Drawings

PROCESS FOR PREPARING ANTHOCYANS FROM CORRESPONDING FLAVONOID GLYCOSIDES

BACKGROUND OF THE INVENTION

The value of anthocyans as a coloring agent for food is becoming more and more valuable while many synthetic coloring agents have been identified hazardous to human bodies.

The hitherto known processes for reductively preparing anthocyans from flavonoid glycosides prior to the present invention are either complex in their operational steps, hazardous to the public or the methods produce poor yields.

SUMMARY OF THE INVENTION

The present invention relates to an improved process for preparing anthocyans by reducing their corresponding flavonoid glycosides with a mtal and acid in which the reduction reaction is conducted either by irradiation of light at 20°–30° C. under acidic conditions or at 20°–30° C. under acidic conditions. The anthocyans are then isolated in the form of a metal salt by neutralizing the reaction solution.

DETAILED DESCRIPTION

This invention relates to a process for preparing anthocyans from flavonoid glycosides, more particularly, it relates to an improved process for reducing corresponding flavonoid glycosides with a metal and acid without causing the destruction of their glycoside structure. It is an object of this invention to provide highly purified anthocyans in good yields by a relatively simple route.

Anthocyans are very unstable pigments found in flowers, fruits and leaves of plants and have in common the basic structure represented by a following formula:

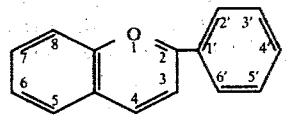

The methods of preparing of anthocyans are roughly classifiable into: (1) extracting from plants, (2) totally synthesizing them from aromatic phenols or aldehydes and (3) removing an oxygen atom from the 4 position of flavonoid glycosides by reduction. Of these processes, the process (1) requires a complex step for isolating and refining the anthocyans and the process (2) requires many steps, thus it is expensive to produce anthocyans in a pure condition by these processes. The process (3) is attainable through one relatively simple step, and thus it has been under serious investigation by the present inventors.

The hitherto known processes of reducing flavonols were conducted, for example, in such a manner that a metal and acid or sodium amalgam or lithium alminum hydride were employed however, the employment of sodium amalgam, a mercurial compound, is not preferable from the viewpoint of its hazards to the public and further undesirable 4-oxyflavones are produced much more frequently during these reduction processes than an expected flavylium salt. On the other hand, the employment of lithium alminium hydride in such processes gives an average yield rate of 29%, however, it is necessary to convert the flavonol used therein to its soluble derivative by means of an organic solvent.

With regard to the reduction of flavonols by means of a metal and acid, it has been reported that the pelargonidin chloride was obtained from kaemferol by reductive acetylation with zinc dust, which resulted in a yield rate of 40.8% by a spectroscopic determination. However, no isolation step thereof was reported in this process, and further, a hydrolysing step for removing acetyl groups was required for obtaining the free form of anthocyan in this reduction reaction.

With regard to reduction of flavonols with magnesium and hydrochloric acid, it has been reported that the isolation of the objective anthocyan was using such complex means that has been applied to the isolation and refinement of some ingredients from plant bodies yield low results. For example, by using a lead salt or picric acid as a refining agent or by using chromatographical means, a yield of not more than 2% of the objective compound is obtained.

One of the processes for reducing flavonoid glycosides with a metal and acid in the present invention is characterized by carrying out the reduction under light irradiation under acidic conditions and the other is characterized by carrying out the reduction at under 30° C. and then isolating the produced anthocyans in the form of a metal salt, under neutral conditions.

To explain the one process of the present invention, a metal and acid therein are employed and selected from those combinations which may generate hydrogen, for example, zinc dust and hydrochloric acid, and magnesium powders and hydrochloric acid. A flavonoid glycoside is dissolved in a polar solvent such as methanol and ethanol and a metal is added, then an acid is added dropwise to the solution under irradiation of light at 20°–30° C. while stirring taking caution to always maintain the reaction solution acidic and the temperature within said range with the acid of a cooling agent if necessary. The metal and acid may also be added alternately in a small quantities of each. After a prescribed quantities of the acid is added, the irradiation of light is continued for some hours at about 10° C. while stirring and it is recommended to blow air into the reaction mixture to increase the yield of the objective anthocyan compound. The anthocyan is precipitated in fine crystalline form, which is collected and recrystallized from water or a non-polar solvent or polar solvent and hydrochloric acid. The thus-obtained anthocyan is identified by the TLC method and includes less than 3 ppm of metal impurities such as magnesium. The irradiation of light is conveniently conducted with an ordinary incandescent lamp, an artificial sun lamp or an ultraviolet lamp.

The yield rate of this process averages about 20–30% of the objective compound in comparison with 4.6% when no irradiation step is applied to the process.

To explain the other process of this invention, a flavonoid glycoside is dissolved in a polar solvent and a metal is added and an acid such as concentrated hydrogen chloride is added dropwise to the solution at 20°–30° C. while stirring taking caution so as to always maintain the solution acidic and not to exceed a temperature over 30° C. If the temperature is over 30° C., hydrolysis of the glycoside occurs and causes a decrease in the yield rate of the objective anthocyan. After addition of a prescribed quantity of the acid, stirring is continued until the reduction is completed. The reaction solution is neutralized with an aqueous alkali like aqueous ammonia at under 10° C., to which a hydrophylic solvent like acetone is added. The anthocyan, which precipitates in the form of a metal salt, which is then collected. The collected product is treated with concentrated hydrochloric acid at below room temperature while stirring to isolate the free anthocyan from its salt. The isolated anthocyan is then washed with or in diluted hydrochloric acid and is recrystallized from water or a polar or non-polar organic solvent and hydrochloric acid. The thus obtained anthocyan is identified to be free of organic impurities by the TLC or a paper chromatography method and to include not more than 30 ppm of metallic impurities, such as magnesium. It is more recommendable for the purpose of producing good yields to use aqueous ammonia as a neutralizer as opposed to the use of aqueous caustic soda or aqueous potash. Further, the use of hydrochloric acid in the aforementioned decomposition step of the metal salt is much more preferable than to use other kinds of acids because the acids other than hydrochloric acid are likely to prolong the deposition time of the anthocyan or result in poor yields of the objective anthocyan compound.

The average yield rate of this process is 10–20%, which is far better than those of the aforestated known processes.

The following specific examples serve to illustrate the present invention but are not intended to limit the same.

EXAMPLE 1

To 250 liters of methanol, 25 Kg of rutin, one of the glycosides of quercetin, was dissolved and 12.5 Kg of magnesium was added. 125 liters of concentrated hydrochloric acid was added dropwise into the solution over a period of 3.5–4.0 hours under light irradiation by means of a sun lamp so as to maintain the reaction temperature at 20°–30° C. with the aid of dry ice and isopropanol. After the hydrochloric acid is added, 25 g of a seed crystal was added to the reaction mixture and was stirred for about 5 hours at under 10° C. while irradiating with light. The deposition of keracyanin crystals began after 75 minutes from the beginning of the stirring. The deposited crystals were collected by filtration and was washed with 10% hydrochloric acid and acetone and was dried by air at under 40° C., which gave 5.85 Kg (23.4%) of crude keracyanin. The crude crystal was recrystallized from water and concentrated hydrochloric acid and was dried at under 40° C., which gave 5.27 Kg (21.1%) of the objective compound. The same process without the irradiation step gave a keracyanin yield of only 4.6%.

EXAMPLE 2

To 50 ml of methanol, 5.0 g of myricitrin, one of the glycosides of myricetin, was dissolved and 2.5 g of magnesium powders were added. Concentrated hydrochloric acid was added dropwise to the solution under irradiation by means of an incandescent light at a solution temperature of 20°–30° C. After the reduction reaction completed, 100 ml of water was added to the reaction mixture and the irradiation was continued for 5 hours while stirring. The thus-deposited delphinidin-3-rhamnoside was collected by filtration, which was washed with diluted hydrochloric acid and was dried in a dessicator on sodium hydroxide. The yield was 1.5 g (30%).

EXAMPLE 3

The compound delphinidin 3-rhamnoside was prepared by a method similar to that described in Example 2 with an additional step of blowing air into the reaction mixture using an air pump during the aforementioned 5 hours stirring, which gave 1.7 g (34%) of the objective anthocyan compound.

EXAMPLE 4

To 200 ml of methanol, 20 g of rutin was dissolved and 10 g of magnesium was added. 100 ml of concentrated hydrochloric acid was added dropwise to the solution over a period of about one hour so as to maintain the reaction temperature at 20°–30° C. with the aid of ice and sodium chloride. After the dropwise addition of hydrochloric acid was completed, the reaction mixture was stirred for 30 minutes, into which 36 ml of concentrated aqueous ammonia was dropped at 0°–10° C. under stirring, then the solution became blue. 600 ml of acetone was added to the blue solution and the magnesium salt of keracyanin precipitated which was collected by filtration. The collected material was added to 50 ml of concentrated hydrochloric acid, which was stirred for 3 hours at room temperature and was collected by filtration. The collected material was again dispersed in 18% hydrochloric acid, was collected, and then dissolved in 25 ml of dimethylformamide and was filtered 15 minutes later. 60 ml of concentrated hydrochloric acid was slowly added to the filtrate at 0°–10° C., and stirred for one hour. The deposited keracyanin was collected by filtration and was washed with diluted hydrochloric acid and was dried in vacuo in a dessicator. The yield was 2.5 g (12.5%).

EXAMPLE 5

To 2000 liters of methanol, 200 g of myricitrin was dissolved and 100 g of magnesium was added. One liter of concentrated hydrochloric acid was added dropwise to the solution over a period of about 2 hours so as to maintain the reaction temperature at 20°–30° C. with the aid of ice and sodium chloride. After the dropwise addition of hydrochloric acid was completed, the reaction mixture was stirred for about one hour and was cooled to 0°–10° C. 300 ml of concentrated aqueous ammonia was added dropwise to the reaction mixture under stirring and 6 liters of acetone was added. The precipitate formed from such reaction was collected by filtration, which was dispersed in 500 ml of cooled concentrated hydrochloric acid and was stirred for 3 hours at room temperature and was collected. The collected material was again dispersed in one liter of diluted hydrochloric acid, which was stirred for one hour at 20°–30° C. and was collected by filtration. The collected material was dissolved in 230 ml of dimethylformamide and was filtered. The filtrate was added to 1.5 times the quantity of concentrated hydrochloric acid, which was stirred for 2 hours, and deposition of keracyanin occurred. The thus deposited keracyanin was collected and was washed with dilute hydrochloric acid then with a mixture of acetone and ethyl acetate and was dried in a dessicator. The yield of the objective compound was 30 g (15%).

What is claimed is:

1. A process for preparing anthocyans from their corresponding flavonoid glycosides which comprises reducing the flavonoid glycosides with concentrated hydrochloric acid and a metal selected from the group consisting of magnesium and zinc at temperatures not higher than 30° C. under acidic conditions, precipitating the anthocyans formed from said reduction reaction as a metal salt by neutralizing the reaction solution with an alkali and isolating the free anthocyans by decomposing said metal salt with concentrated hydrochloric acid.

2. A process in accordance with claim 1, wherein said flavonoid glycosides are selected from the group consisting of rutin and myricitrin.

3. A process in accordance with claim 1, wherein the alkali employed as a neutralizer is aqueous ammonia.

* * * * *